US 9,409,956 B2

(12) United States Patent
Kopecko et al.

(10) Patent No.: US 9,409,956 B2
(45) Date of Patent: Aug. 9, 2016

(54) SALMONELLA TYPHI TY21A EXPRESSING YERSINIA PESTIS F1-V FUSION PROTEIN AND USES THEREOF

(71) Applicant: The United States of America, as represented by the Secretary, Department of Health and Human Services, Washington, DC (US)

(72) Inventors: Dennis J. Kopecko, Silver Spring, MD (US); Manuel Osorio, Bethesda, MD (US); Monica R. Foote, North Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 79 days.

(21) Appl. No.: 14/402,457

(22) PCT Filed: May 22, 2013

(86) PCT No.: PCT/US2013/042240
§ 371 (c)(1),
(2) Date: Nov. 20, 2014

(87) PCT Pub. No.: WO2013/177291
PCT Pub. Date: Nov. 28, 2013

(65) Prior Publication Data
US 2015/0152144 A1  Jun. 4, 2015

Related U.S. Application Data

(60) Provisional application No. 61/650,676, filed on May 23, 2012.

(51) Int. Cl.
*A61K 39/00* (2006.01)
*A61K 39/112* (2006.01)
(Continued)

(52) U.S. Cl.
CPC ............. *C07K 14/24* (2013.01); *A61K 39/0291* (2013.01); *A61K 39/00* (2013.01); *A61K 2039/523* (2013.01); *C07K 2319/036* (2013.01); *C07K 2319/40* (2013.01)

(58) Field of Classification Search
CPC . A61K 39/0291; A61K 39/00; A61K 39/112; C07K 14/24; C07K 2319/00
USPC .................................. 424/192.1, 190.1, 234.1
See application file for complete search history.

(56) References Cited

U.S. PATENT DOCUMENTS 5,985,285 A * 11/1999 Titball ................... C07K 14/24
424/234.1
7,524,507 B1 * 4/2009 Titball ................. A61K 39/025
424/200.1
(Continued)

FOREIGN PATENT DOCUMENTS

WO   WO 95/18231   7/1995
WO   WO 96/28551   9/1996
(Continued)

OTHER PUBLICATIONS

Foote et al, Cloning and expression of a Y. pestis F1-V fusion protien into *Salmonella* Typhi Ty21a:Part of a combination oral anthrax-plague vaccine, Abstract for the 111th General Meeting of the American Society for Microbiology, published online Apr. 21, 2011.*
(Continued)

*Primary Examiner* — Albert Mavarro
*Assistant Examiner* — Ginny Portner
(74) *Attorney, Agent, or Firm* — Klarquist Sparkman, LLP (57) ABSTRACT

Described herein is the generation of a plasmid construct for expression of a *Yersinia pestis* F1-V fusion protein. In the disclosed plasmid, the F1-V fusion protein coding sequence is operably linked to the *E. coli* htrA promoter, and is fused in-frame to the *E. coli* HlyA secretion signal sequence. Also described is *Salmonella enterica* serovar Typhi strain Ty21a containing the F1-V fusion protein expression plasmid, such as for use as an oral vaccine against plague.

19 Claims, 5 Drawing Sheets

1747 bp Fragment of pHtrF1-V-hly

(51) Int. Cl.
  *C07K 14/24* (2006.01)
  *A61K 39/02* (2006.01)

(56) References Cited

U.S. PATENT DOCUMENTS

| | | | | |
|---|---|---|---|---|
| 7,758,855 B2* | 7/2010 | Kopecko | ............... | A61K 39/07 424/93.2 |
| 7,955,600 B2* | 6/2011 | Hensel | ............... | C12N 15/87 424/184.1 |

FOREIGN PATENT DOCUMENTS

| | | | | |
|---|---|---|---|---|
| WO | 2005/056769 | * | 6/2005 | |
| WO | 2008/039408 | * | 4/2008 | ........... A61K 39/112 |

OTHER PUBLICATIONS

Calhoun and Kwon, "*Salmonella*-based Plague Vaccines for Bioterrorism," *J Microbiol Immunol Infect*, vol. 39:92-97, 2006.

Foote et al., "Cloning and expression of a *Y. pestis* F1-V fusion protein into *Salmonella* Typhi Ty21a: Part of a combination oral anthrax-plague vaccine," Abstract for the 111th General Meeting of the American Society for Microbiology, published online Apr. 21, 2011.

Foote et al., "Cloning and expression of a *Y. pestis* F1-V fusion protein into *Salmonella* Typhi Ty21a: Part of a combination oral anthrax-plague vaccine," Poster for the 111th General Meeting of the American Society for Microbiology, May 24, 2011.

Garmory et al., "Oral Immunisation with Live *aro*A Attenuated *Salmonella enterica* Serovar Typhimurium Expressing the Yersinia pestis V Antigen Protects Mice Against Plague," *Vaccine*, vol. 21:3051-3057, 2003.

Garmory et al., "Antibiotic-Free Plasmid Stabilization by Operator-Repressor Titration for Vaccine Delivery by Using Live *Salmonella enterica* Serovar Typhimurium," *Infect Immunol.*, vol. 73:2005-2011, 2005.

Leary et al., "Expression of an F1/V Fusion Protein in Attenuated *Salmonella typhimurium* and Protection of Mice Against Plague," *Microb Pathog*, vol. 23:167-179, 1997.

Liu et al., "A Comparison of Immunogenicity and Protective Immunity against Experimental Plague by Intranasal and/or Combined with Oral Immunization of Mice with Attenuated *Salmonella* Serovar Typhimurium Expressing Secreted *Yersinia pestis* F1 and V antigen," *FEMS Immunol Med Microbiol*, vol. 51:58-69, 2007.

Morton et al., "A *Salmonella enterica* Serovar Typhi Vaccine Expressing *Yersinia pestis* F1 Antigen on its Surface Provides Protection Against Plague in Mice," Vaccine, vol. 22:2524-2532, 2004.

Osorio et al., "Anthrax Protective Antigen Delivered by *Salmonella enterica* Serovar Typhi Ty21a Protects Mice from a Lethal Anthrax Spore Challenge," *Infect Immun*, vol. 77:1475-1482, 2009.

Ramirez et al., "Mucosally Delivered *Salmonella* Typhi Expressing the *Yersinia pestis* F1 Antigen Elicits Mucosal and Systemic Immunity Early in Life and Primes the Neonatal Immune System for a Vigorous Anamnestic Response to Parenteral F1 Boost," *J Immunol*, vol. 182:1211-1222, 2009.

Sizemore et al., "Construction and Screening of Attenuated ΔphoP/Q *Salmonella typhimurium* Vectored Plague Vaccine Candidates," *Human Vaccin Immunother*, vol. 8:371-383, 2012.

Sun et al., "Developing Live Vaccines against *Yersinia pestis*," *J Infect Dev Ctries*, vol. 5:614-627, 2011.

Torres-Escobar et al., "Fine-Tuning Synthesis of *Yersinia pestis* LcrV from Runaway-Like Replication Balanced-Lethal Plasmid in a *Salmonella enterica* Serovar Typhimurium Vaccine Induces Protection against a Lethal *Y. pestis* Challenge in Mice," *Infect Immun*, vol. 78:2529-2543, 2010.

Yamamoto et al., "Enteroadhesion Fimbriae and Enterotoxin of *Escherichia coli*: Genetic Transfer to a Streptomycin-Resistant Mutant of the *galE* Oral-Route Live-Vaccine *Salmonella typhi* Ty21a," *Infect Immun*, vol. 50:925-928, 1985.

Yang et al., "Oral Vaccination with *Salmonella* Simultaneously Expressing *Yersinia pestis* F1 and V Antigens Protects against Bubonic and Pneumonic Plague," *J Immunol*, vol. 178:1059-1067, 2007.

* cited by examiner

FIG. 1

1747 bp Fragment of pHtrF1-V-hly

Anti-F1

| | F1-V S | F1-V P | PA S |
|---|---|---|---|
| 100 | | | |
| 80 | | | |
| 60 | ■ | | |
| 50 | | | |
| 40 | | | |

Anti-V

| | F1-V S | F1-V P | PA S |
|---|---|---|---|
| 100 | | | |
| 80 | | | |
| 60 | ■ | | |
| 50 | | | |
| 40 | | | |

SALMONELLA TYPHI TY21A EXPRESSING YERSINIA PESTIS F1-V FUSION PROTEIN AND USES THEREOF

CROSS REFERENCE TO RELATED APPLICATIONS

This is the U.S. National Stage of International Application No. PCT/US2013/042240, filed May 22, 2013, published in English under PCT Article 21(2), which claims the benefit of U.S. Provisional Application No. 61/650,676, filed May 23, 2012, which is herein incorporated by reference in its entirety.

FIELD

This disclosure concerns the development of immunogenic compositions for protection against *Yersinia pestis*, the causative agent of plague. This disclosure further concerns *Salmonella* Typhi strain Ty21a harboring a F1-V fusion protein expression construct, and methods of use thereof.

BACKGROUND

*Yersinia pestis* is the causative agent of plague. At least three great pandemics of plague have been recorded in history, which killed nearly 200 million people. Plague is a zoonotic disease typically transmitted by the bite of an infected flea. Natural reservoirs for *Y. pestis* include rodents, squirrels and prairie dogs. Large reservoirs of *Y. pestis* currently exist on all major inhabited continents, except Australia (Sun et al., *J Infect Dev Ctries* 5(9):614-627, 2011). Plague is endemic to many parts of the world, including Africa, China, India, portions of South America and the southwestern United States (Yang et al., *J Immunol* 178:1059-1067, 2007; Leary et al., *Microb Pathog* 23:167-179, 1997). Recent epidemiological studies indicate that worldwide there are approximately 4,000 human plague cases annually (Sun et al., *J Infect Dev Ctries* 5(9):614-627, 2011). Thus, plague remains a serious public health concern.

Plague most commonly presents as bubonic plague, characterized by the sudden onset of fever and painful swelling of lymph nodes ("buboes") close to the flea bite. Prompt treatment with antibiotics is generally effective (Morton et al., *Vaccine* 22:2524-2532, 2004). However, bacteria can disseminate widely from the site of the flea bite and in some cases, infect the lung. If the lung is infected, plague can be transmitted in aerosols produced by coughing or sneezing, leading to outbreaks of primary pneumonic plague (Leary et al., *Microb Pathog* 23:167-179, 1997). Pneumonic plague is highly contagious and generally fatal (Morton et al., *Vaccine* 22:2524-2532, 2004). Since plague is highly infectious and can spread by aerosolization, *Y. pestis* is considered a potential biological weapon (Sun et al., *J Infect Dev Ctries* 5(9): 614-627, 2011; Yang et al., *J Immunol* 178:1059-1067, 2007).

SUMMARY

Disclosed herein is the generation of a plasmid construct for expression of a *Yersinia pestis* F1-V fusion protein. Also disclosed are *Salmonella enterica* serovar Typhi strain Ty21a (referred to as "*Salmonella* Typhi Ty21a" or "Ty21a") bacteria comprising the disclosed plasmid construct, such as for use as a vaccine against plague.

Provided herein is a recombinant nucleic acid molecule comprising a *Yersinia pestis* F1-V fusion protein coding sequence operably linked to an inducible promoter that is active in eukaryotic host cells, such as the *Escherichia coli* htrA promoter. In some embodiments, the nucleic acid molecule comprises a sequence at least 85% identical to nucleotides 1-1558 of SEQ ID NO: 1. In some embodiments, the nucleic acid molecule further includes a secretion signal peptide coding sequence, such as the *E. coli* HlyA secretion signal sequence, fused in-frame with the F1-V fusion protein coding sequence. In particular non-limiting examples, the nucleic acid molecule comprises the sequence of SEQ ID NO: 1.

Also provided are plasmids comprising the disclosed nucleic acid molecules, and *Salmonella* Typhi Ty21a bacteria comprising the disclosed nucleic acid molecules or plasmids.

In one non-limiting embodiment, provided is a recombinant nucleic acid molecule comprising a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence, wherein the sequence of the nucleic acid molecule comprises SEQ ID NO: 1. Also provided is a plasmid comprising the nucleic acid molecule, an origin of replication, a selectable marker and the *E. coli* HlyB and HlyD protein coding sequences. Further provided is a *Salmonella* Typhi Ty21a comprising the plasmid.

Also provided are immunogenic compositions including *Salmonella* Typhi Ty21a containing an F1-V expression plasmid and a pharmaceutically acceptable carrier.

Further provided by the present disclosure is a method of eliciting an immune response against *Yersinia pestis* in a subject by administering to the subject *Salmonella* Typhi Ty21a containing an F1-V expression plasmid, or administering an immunogenic composition disclosed herein. Also provided is a method of preventing plague, reducing the risk of developing plague or treating plague in a subject by administering to the subject *Salmonella* Typhi Ty21a containing a plasmid or recombinant nucleic acid molecule disclosed herein, or administering an immunogenic composition as disclosed herein.

The foregoing and other objects, features, and advantages of the invention will become more apparent from the following detailed description, which proceeds with reference to the accompanying figures.

BRIEF DESCRIPTION OF THE DRAWINGS

*Salmonella* Typhi Ty21a transformed with pHtrF1-V-hly produces and secretes the F1-V fusion protein (58 kDa).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 7, 2014, 13.7 KB, which is incorporated by reference herein. In the accompanying sequence listing:

SEQ ID NO: 1 is the nucleotide sequence of the F1-V fusion DNA insert cloned into plasmid pHtrF1-V-Hly. SEQ ID NO: 1 contains the following elements:
 nucleotides 1-112=htrA promoter sequence
 nucleotides 113-562=F1 antigen coding sequence
 nucleotides 563-580=linker sequence
 nucleotides 581-1558=V antigen coding sequence
 nucleotides 1559-1747=HlyA secretion signal sequence
 SEQ ID NO: 2 is the amino acid sequence of the F1 antigen.
 SEQ ID NO: 3 is the amino acid sequence of the linker peptide.
 SEQ ID NO: 4 is the amino acid sequence of the V antigen.
 SEQ ID NO: 5 is the amino acid sequence of the HlyA secretion signal peptide.

DETAILED DESCRIPTION

I. Abbreviations

CFU colony forming unit
ELISA enzyme-linked immunosorbent assay
F1 fraction 1 antigen
IFN interferon
IL interleukin
i.p. intraperitoneal
ORI origin of replication
PA protective antigen
SDS-PAGE sodium dodecyl sulfate-polyacrylamide gel electrophoresis
TNF tumor necrosis factor
V virulence antigen II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: To give, apply or bring a composition into contact with a subject. Administration can be accomplished by any of a number of routes, such as, for example, topical, oral, subcutaneous, intramuscular, intraperitoneal, intravenous, intrathecal and intramuscular. In some embodiments described herein, an immunogenic composition is administered to a subject by an oral route.

Coding sequence: A nucleic acid sequence that encodes a protein or peptide (i.e. contains an open reading frame).

F1 antigen: A *Yersinia pestis* virulence protein. F1 antigen is encoded by a 100 kb plasmid unique to *Y. pestis* and is the major protein component of the capsule encompassing *Y. pestis* bacilli. The F1 antigen is thought to prevent phagocytosis by host cells. The F1 antigen is also referred to as the "F1 capsular antigen." F1 sequences are known and are publically available (for instance in the GenBank database). An exemplary F1 antigen nucleotide sequence is set forth herein as nucleotides 113-562 of SEQ ID NO: 1; and an exemplary F1 amino acid sequence is provided as SEQ ID NO: 2.

Fused in-frame: Refers to two nucleic acid sequences that are joined such that they are in the same reading frame.

Fusion protein: A protein generated by expression of a nucleic acid sequence engineered from nucleic acid sequences encoding at least a portion of two different proteins. To create a fusion protein, the nucleic acid sequences must be in the same reading frame ("in-frame") and contain no internal stop codons.

HlyB and HlyD: Prokaryotic hemolysin secretion proteins. In some embodiments herein, the disclosed plasmids encode *E. coli* HlyB and HlyD proteins. A low-copy plasmid (pGB-2) encoding *E. coli* HlyB and HlyD has been previously described in U.S. Pat. No. 7,758,855, which is herein incorporated by reference.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunize: To render a subject protected from a disease (for example, an infectious disease), such as by vaccination.

Immunogenic composition: A term used herein to mean a composition useful for stimulating or eliciting a specific immune response (or immunogenic response) in a subject. In some embodiments herein, the immunogenic composition includes a *Salmonella* Typhi Ty21a containing an F1-V expression plasmid. In some embodiments, the immunogenic response is protective or provides protective immunity, in that it enables the subject to better resist infection with *Yersinia pestis*, or disease progression from *Yersinia pestis* (e.g., bubonic or pneumonic plague). One specific example of a type of immunogenic composition is a vaccine.

In some embodiments, an "effective amount" or "immune-stimulatory amount" of an immunogenic composition is an amount which, when administered to a subject, is sufficient to engender a detectable immune response. Such a response may comprise, for instance, generation of an antibody specific to one or more of the epitopes provided in the immunogenic composition. Alternatively, the response may comprise a T-helper or CTL-based response to one or more of the epitopes provided in the immunogenic composition. All three of these responses may originate from naïve or memory cells. In other embodiments, a "protective effective amount" of an immunogenic composition is an amount which, when administered to an animal, is sufficient to confer protective immunity upon the animal (such as protection against plague).

Isolated: An "isolated" or "purified" biological component (such as a nucleic acid, peptide or protein) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Open reading frame (ORF): A series of nucleotide triplets (codons) coding for amino acids without any internal termination codons. These sequences are usually translatable into a peptide/polypeptide/protein/polyprotein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Origin of replication (ORI): A particular nucleic acid sequence in a genome or plasmid where DNA replication is initiated. The specific structure of an ORI varies by species, but all are generally characterized by a high AT content.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plague: An infectious disease caused by *Yersinia pestis*, which is a non-motile, slow-growing facultative bacteria in the family Enterobacteriacea. *Y. pestis* is carried by rodents, particularly rats, and in the fleas that feed on them. Other animals and humans usually contract the bacteria directly from rodent or flea bites. Infection with *Y. pestis* can result in bubonic plague, septicemic plague or pneumonic plague.

In bubonic plague, which is the most common form of *Y. pestis*-induced disease, bacteria infect the lymphatic system, which becomes inflamed. Bubonic plague is typically contracted by the bite of an infected flea or rodent. In rare cases, *Y. pestis* bacteria, from a piece of contaminated clothing or other material used by a person with plague, enter through an opening in the skin. Bubonic plague affects the lymph nodes, and within three to seven days of exposure to the bacteria, flu-like symptoms develop such as fever, headache, chills, weakness, and swollen, tender lymph glands (buboes). Bubonic plague is rarely spread from person to person.

Septicemic plague is contracted the same way as bubonic plague, usually through a flea or rodent bite, and the bacteria multiply in the blood. However, septicemic plague is characterized by the occurrence of multiplying bacteria in the bloodstream, rather than just the lymph system. Septicemic plague usually occurs as a complication of untreated bubonic or pneumonic plague, and its symptoms include fever, chills, weakness, abdominal pain, shock, and bleeding underneath the skin or other organs. Buboes, however, do not develop in septicemic plague, and septicemic plague is rarely spread from person to person.

Pneumonic plague is the most serious form of plague and occurs when *Y. pestis* bacteria infect the lungs and cause pneumonia. Pneumonic plague can be contracted when *Y. pestis* bacteria are inhaled. Within one to three days of exposure to airborne droplets of pneumonic plague, fever, headache, weakness, rapid onset of pneumonia with shortness of breath, chest pain, cough, and sometimes bloody or watery sputum develop. This type of plague also can be spread from person to person when bubonic or septicemic plague goes untreated after the disease has spread to the lungs. At this point, the disease can be transmitted to someone else by *Y. pestis-carrying* respiratory droplets that are released into the air when the infected individual coughs or sneezes.

Plasmid: A circular nucleic acid molecule capable of autonomous replication in a host cell. In some embodiments of the present disclosure, the plasmid is a low-copy number plasmid. For example, the low-copy number plasmid can be a plasmid that produces approximately 1-10, such as 3-9 or 5-7 copies of the plasmid in a host cell. In particular examples, the low-copy number plasmid produces approximately 5-7 copies in a host cell. In specific examples, the low-copy number plasmid is based on the pGB-2 plasmid as described in U.S. Pat. No. 7,758,855, which is herein incorporated by reference.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: An array of nucleic acid control sequences that directs transcription of a nucleic acid. A promoter includes necessary nucleic acid sequences near the start site of transcription. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987). In some embodiments herein, the promoter is the promoter of the htrA (high-temperature requirement A) gene of *E. coli*. The htrA promoter is an inducible promoter active during *Salmonella* infection of eukaryotic cells. In specific non-limiting examples, the htrA promoter sequence comprises nucleotides 1-112 of SEQ ID NO: 1.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

*Salmonella enterica*: A gram-negative, rod-shaped, flagellated bacterium. The *S. enterica* species includes more than 2500 different serovars, one of which is the *Salmonella* Typhi serovar.

*Salmonella* Typhi Ty21a: Ty21a is a strain of the *Salmonella enterica* serovar *Salmonella* Typhi. Ty21a is a live attenuated bacterial strain that is used as an oral vaccine against typhoid (Osorio et al., *Infect Immun* 77(4):1475-1482, 2009; Germanier and Furer, *J Infect Dis* 131:553-558, 1975; Wandan et al., *Bull WHO* 58:469-474, 1980; U.S. Pat. No. 3,856,935).

Selectable marker: A nucleotide sequence that encodes a protein that confers a positive or negative selection advantage to the organism (such as a bacterium) that expresses the marker. Selectable markers include, for example, antibiotic resistance genes, such as spectinomycin.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Pearson and Lipman, *Proc. Natl. Acad. Sci. U.S.A.* 85:2444, 1988; and Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

In some embodiments herein, provided are nucleotide or amino acid sequences at least 80%, at least 85%, at least 90%, at least 95%, at least 96%, at least 97%, at least 98% or at least 99% identical to any one of SEQ ID NOs: 1-5.

Serovar: A subdivision of a species or subspecies distinguished by a characteristic set of antigens. A serovar is also referred to as a "serotype."

Signal peptide: A short (typically 3-60 amino acids in length) peptide chain that directs the post-translational transport of a protein. A secretion signal peptide is a signal peptide that directs a protein for secretion from the cell in which it is produced. In some embodiments herein, the secretion signal peptide is the signal peptide from the *E. coli* hemolysin protein HlyA. In specific non-limiting examples, the HlyA secretion signal peptide has the amino acid sequence of SEQ ID NO: 5, and is encoded by nucleotides 1559-1747 of SEQ ID NO: 1.

Subject: Living multi-cellular vertebrate organisms, a category that includes both human and non-human mammals.

Therapeutically effective amount: A quantity of a specified agent sufficient to achieve a desired effect in a subject being treated with that agent. For example, this may be the amount of *Salmonella* Typhi Ty21a containing an F1-V expression plasmid useful for eliciting an immune response in a subject and/or for preventing infection by *Yersinia pestis*. Ideally, in the context of the present disclosure, a therapeutically effective amount of *Salmonella* Typhi Ty21a containing an F1-V expression plasmid is an amount sufficient to increase resistance to, prevent, ameliorate, and/or treat infection caused by *Yersinia pestis* in a subject without causing a substantial cytotoxic effect in the subject. The effective amount of *Salmonella* Typhi Ty21a containing an F1-V expression plasmid useful for increasing resistance to, preventing, ameliorating, and/or treating infection in a subject will be dependent on, for example, the subject being treated, the manner of administration of the therapeutic composition and other factors.

Unit dose: A physically discrete unit containing a predetermined quantity of an active material calculated to individually or collectively produce a desired effect such as an immunogenic effect. A single unit dose or a plurality of unit doses can be used to provide the desired effect, such as an immunogenic effect. In one example, a unit dose includes a desired amount of *Salmonella* Typhi expressing an F1-V fusion protein as disclosed herein.

V antigen: A *Yersinia pestis* virulence protein encoded by the lcrV gene. V antigen is a secreted protein that plays a multifunctional role in *Y. pestis* virulence. For example, V antigen is a positive regulator for expression of low calcium response virulence genes and is involved in the translocation of effector proteins into eukaryotic cells via the type II secretion system. V antigen is also thought to function as an immunomodulator by inhibiting the production of cytokines such as IFN-γ and TNF-α. V antigen sequences are known and are publically available. An exemplary V antigen nucleotide sequence is provided herein as nucleotides 581-1558 of SEQ ID NO: 1; and an exemplary V antigen amino acid sequences is set forth herein as SEQ ID NO: 4.

Vaccine: An immunogenic composition that can be administered to a subject (such as a veterinary or human subject) to confer immunity, such as active immunity, to a disease or other pathological condition (such as plague). Vaccines can be used therapeutically or prophylactically. Thus, vaccines can be used to reduce the likelihood of infection or to reduce the severity of symptoms of a disease or condition or limit the progression of the disease or condition. In one example herein, the vaccine comprises *Salmonella* Typhi expressing an F1-V fusion protein as disclosed herein.

*Yersinia pestis*: A Gram-negative, rod-shaped bacterium. *Y. pestis* is a facultative anaerobe capable of infecting humans and other animals. Infection with *Y. pestis* can cause bubonic, septicemic or pneumonic plague.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the development of a plasmid construct for expression of a *Yersinia pestis* F1-V fusion protein. Also disclosed is *Salmonella enterica* serovar Typhi strain Ty21a (referred to herein as "*Salmonella* Typhi Ty21a" or "Ty21a") containing the F1-V fusion protein expression plasmid, such as for use as an oral vaccine against plague.

Provided herein is a recombinant nucleic acid molecule comprising a *Yersinia pestis* F1-V fusion protein coding sequence operably linked to an *Escherichia coli* htrA promoter sequence. The htrA promoter is an inducible promoter active in eukaryotic host cells. In some instances, the coding regions of the F1 and V proteins are separated by a nucleic acid linker, such as a linker comprising nucleotides 563-580 of SEQ ID NO: 1.

In some embodiments, the F1-V fusion protein coding sequence is at least 85%, at least 90%, at least 95%, at least 96%, at least 97%, at least 98% or at least 99% identical to nucleotides 113-1558 of SEQ ID NO: 1. In particular examples, the F1-V fusion protein coding sequence comprises or consists of nucleotides 113-1558 of SEQ ID NO: 1.

In some embodiments, the htrA promoter sequence is at least 85%, at least 90%, at least 95%, at least 96%, at least 97%, at least 98% or at least 99% identical to nucleotides 1-112 of SEQ ID NO: 1. In particular examples, the htrA promoter sequence comprises or consists of nucleotides 1-112 of SEQ ID NO: 1.

In some embodiments, the nucleic acid molecule comprising a *Y. pestis* F1-V fusion protein coding sequence operably linked to an *E. coli* htrA promoter sequence comprises a sequence at least 85%, at least 90%, at least 95%, at least 96%, at least 97%, at least 98% or at least 99% identical to nucleotides 1-1558 of SEQ ID NO: 1. In particular examples, the nucleic acid molecule comprises or consists of nucleotides 1-1558 of SEQ ID NO: 1.

In some embodiments, the recombinant nucleic acid molecule further comprises a secretion signal peptide coding sequence fused in-frame with the F1-V fusion protein coding sequence. In some examples, the secretion signal peptide is the *E. coli* HlyA secretion signal peptide. In specific non-limiting examples, the *E. coli* HlyA secretion signal peptide coding sequence is at least 85%, at least 90%, at least 95%, at least 96%, at least 97%, at least 98% or at least 99% identical to nucleotides 1559-1747 of SEQ ID NO: 1, or comprises or consists of nucleotides 1559-1747 of SEQ ID NO: 1.

In particular embodiments, the sequence of the recombinant nucleic acid molecule is at least 85%, at least 90%, at least 95%, at least 96%, at least 97%, at least 98% or at least 99% identical to SEQ ID NO: 1. In specific non-limiting examples, the sequence of the nucleic acid molecule comprises or consists of SEQ ID NO: 1.

Further provided is a plasmid comprising a recombinant nucleic acid molecule disclosed herein. Thus, in some embodiments, the plasmid comprises a nucleic acid molecule that is at least 85%, at least 90%, at least 95%, at least 96%, at least 97%, at least 98% or at least 99% identical to SEQ ID NO: 1, or comprises SEQ ID NO: 1.

In some embodiments, the plasmid is a low-copy number plasmid. For example, the low-copy number plasmid can be a plasmid that produces approximately 1-10, or 3-9, or 5-7 copies of the plasmid in a host cell. In particular examples, the low-copy number plasmid produces approximately 5-7 copies in a host cell. In specific examples, the low-copy number plasmid is based on the pGB-2 plasmid as described in U.S. Pat. No. 7,758,855, which is herein incorporated by reference.

In some embodiments, the plasmid further comprises a selectable marker. Selectable markers are well known in the art and a suitable selectable marker can be selected by one of skill in the art based on the desired selection criteria and specific use of the plasmid. In some examples, the selectable marker is an antibiotic resistance gene. In one non-limiting example, the selectable marker is a spectinomycin resistance gene.

In some embodiments, the plasmid further comprises the *E. coli* HlyB and HlyD protein coding sequences. The HlyB and HlyD proteins are hemolysin secretion proteins that enable extracellular secretion of the F1-V fusion protein encoded by the plasmid.

Further provided are *Salmonella* Typhi Ty21a bacteria comprising a recombinant nucleic acid molecule or plasmid disclosed herein. *Salmonella* Typhi Ty21a is a live attenuated bacterial strain that is approved as an oral vaccine for typhoid. Administration of *Salmonella* Typhi Ty21a has been shown to be safe, and this strain has been previously used effectively to express *Bacillus anthracis* protective antigen (PA) (see, for example, Osorio et al., *Infect Immun* 77(4):1475-1482, 2009; and U.S. Pat. No. 7,758,855, which are herein incorporated by reference). Disclosed herein is the use of *Salmonella* Typhi Ty21a bacteria as a carrier to deliver cloned F1 and V antigens (as a fusion protein) of *Yersinia pestis*.

Also provided are immunogenic compositions comprising *Salmonella* Typhi Ty21a containing a plasmid or recombinant nucleic acid molecule disclosed herein, and a pharmaceutically acceptable carrier. In some embodiments, the immunogenic compositions are formulated for oral administration. In some embodiments, the immunogenic compositions are formulated in unit dose form.

Further provided is a method of eliciting an immune response against *Yersinia pestis* in a subject by administering to the subject *Salmonella* Typhi Ty21a bacteria containing a plasmid or recombinant nucleic acid molecule disclosed herein, or administering an immunogenic composition as disclosed herein. In some embodiments, the immune response is a protective immune response. In some embodiments, the *Salmonella* Typhi Ty21a or the immunogenic composition is administered therapeutically, such as after infection by *Y. pestis*. In other embodiments, the *Salmonella* Typhi Ty21a or the immunogenic composition is administered prophylactically, such as to prevent or reduce the risk of infection by *Y. pestis*.

Also provided is a method of preventing plague, reducing the risk of developing plague or treating plague in a subject by administering to the subject a *Salmonella* Typhi Ty21a containing a plasmid or recombinant nucleic acid molecule disclosed herein, or administering an immunogenic composition as disclosed herein. The plague can be bubonic plague, septicemic plague or pneumonic plague. In some embodiments, the *Salmonella* Typhi Ty21a or the immunogenic composition is administered therapeutically, such as after clinical signs of the plague have developed in the subject. In other embodiments, the *Salmonella* Typhi Ty21a or the immunogenic composition is administered prophylactically, such as to prevent or reduce the risk of plague.

In one non-limiting example, provided herein is a recombinant nucleic acid molecule comprising a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence, wherein the sequence of the nucleic acid molecule comprises SEQ ID NO: 1.

In another non-limiting example, provided is a plasmid comprising (i) a recombinant nucleic acid molecule comprising a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence, wherein the sequence of the nucleic acid molecule comprises SEQ ID NO: 1; (ii) an origin of replication; (iii) a selectable marker; and (iv) the *E. coli* HlyB and HlyD protein coding sequences.

In another non-limiting example, provided is a *Salmonella* Typhi Ty21a comprising a recombinant nucleic acid molecule or plasmid, wherein the recombinant nucleic acid molecule or plasmid comprises a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence, wherein the sequence of the nucleic acid molecule or plasmid comprises SEQ ID NO: 1. Further provided is an immunogenic composition comprising the *Salmonella* Typhi Ty21a and a pharmaceutically acceptable carrier. In some instances, the immunogenic composition is formulated for oral administration. Also provided is a method of eliciting an immune response against *Y. pestis* in a subject by administering to the subject the *Salmonella* Typhi Ty21a, or the immunogenic composition.

In yet another non-limiting example, provided is an oral vaccine for protection against plague, wherein the vaccine comprises a recombinant nucleic acid molecule or plasmid, wherein the recombinant nucleic acid molecule or plasmid comprises a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence, wherein the sequence of the nucleic acid molecule or plasmid comprises SEQ ID NO: 1.

The recombinant nucleic acid molecules and plasmids disclosed herein, as well as the *Salmonella* Typhi Ty21a comprising the recombinant nucleic acid molecules or plasmids disclosed herein, have several advantages over previously described vaccines for plague. For example, the *E. coli* htrA promoter is primarily active in vivo, allowing for efficient expression of the F1-V fusion protein in mammalian host cells, while limiting expression in broth culture, which promotes stability of the expression construct for vaccine production. Efficient expression of F1-V in host cells, which enhances the immune response elicited in the host, increases the efficacy of the vaccine. In addition, using a low-copy plasmid, such as the pGB-2 plasmid, further enhances the stability of the F1-V expression construct. Furthermore, use of the *E. coli* HlyA secretion signal and *E. coli* HlyB and HlyD protein coding sequences enhances extracellular secretion of the F1-V fusion protein in a host, further improving the immune response elicited by the vaccine. Finally, use of *Salmonella* Typhi Ty21a allows for a safe and efficient means for oral administration of a plague vaccine.

IV. Formulation and Administration of Immunogenic Compositions

The recombinant nucleic acid molecules, plasmids and immunogenic compositions disclosed herein may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immunogenic compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes. In particular embodiments, the immunogenic compositions are administered orally.

The volume of administration will vary depending on the route of administration. Those of ordinary skill in the art will know appropriate volumes for different routes of administration.

Administration can be accomplished by single or multiple doses. The dose administered to a subject in the context of the present disclosure should be sufficient to induce a beneficial therapeutic response over time, such as to prevent Y. pestis infection or the development of plague. The dose required may vary depending on, for example, the age, weight and general health of the subject.

The amount of immunogenic composition in each dose is selected as an amount that induces an immunostimulatory response without significant, adverse side effects. Such amount will vary depending upon which specific composition is employed and how it is administered. Initial doses may range from about 1 µg to about 1 mg, with some embodiments having a range of about 10 µg to about 800 µg, and still other embodiments a range of from about 25 µg to about 500 µg. Following an initial administration of the immunogenic composition, subjects may receive one or several booster administrations, adequately spaced. Booster administrations may range from about 1 µg to about 1 mg, with other embodiments having a range of about 10 µg to about 750 µg, and still others a range of about 50 µg to about 500 µg. Periodic boosters at intervals of 1-5 years, for instance three years, may be desirable to maintain the desired levels of protective immunity.

When administering bacteria as a component of the immunogenic compositions, doses can also be measured by the number of colony forming units (CFU) in a preparation. Thus, in some examples, a therapeutically effective dose of *Salmonella* Typhi Ty21a harboring an F1-V expression construct is at least 100 CFU, at least $10^3$ CFU, at least $10^4$ CFU, at least $10^5$ CFU, at least $10^6$ CFU, at least $10^7$ CFU, at least $10^8$ CFU, or at least $10^9$ CFU, for example 100 CFU to $10^9$ CFU, or $10^3$ CFU to $10^8$ CFU, or $10^4$ CFU to $10^7$ CFU, or $10^5$ CFU to $10^6$ CFU of the *Salmonella* Typhi Ty21a.

Provided herein are pharmaceutical compositions (also referred to as immunogenic or immunostimulatory compositions) which include a therapeutically effective amount of a recombinant nucleic acid molecule, plasmid or *Salmonella* Typhi Ty21a harboring an F1-V expression construct alone or in combination with a pharmaceutically acceptable carrier.

Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The disclosed immunogenic compositions can include other biologically inactive or active agents (or both). For example, the disclosed immunogenic compositions can include adjuvants, carriers, excipients and anti-microbial agents (such as antibiotics).

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

The following examples are provided to illustrate certain particular features and/or embodiments. These examples should not be construed to limit the disclosure to the particular features or embodiments described.

EXAMPLES

Example 1

Plasmid Construction and Analysis of F1-V Expression and Secretion

This example describes the generation of a genetically stable plasmid system for the expression of *Yersinia pestis* capsule protein fraction 1 (F1)/virulence antigen fusion protein precursor (LcrV) fusion protein (referred to as F1-V fusion protein) in *Salmonella* Typhi vaccine strain Ty21a.

Figure 1:
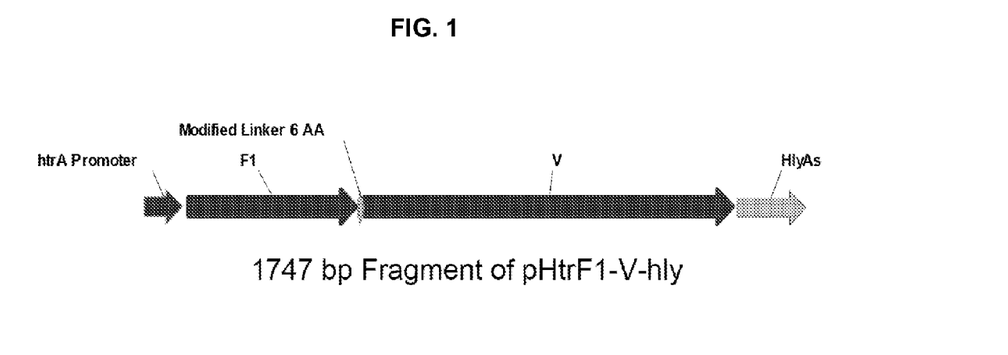
FIG. 1 is a schematic diagram of the synthetic F1-V fusion DNA insert cloned into plasmid pHtrF1-V-Hly.

A genetically stable plasmid expression system for optimized *Bacillus anthracis* protective antigen (PA) expression has been developed previously (see Osorio et al., *Infect Immun* 77(4):1475-1482, 2009; and U.S. Pat. No. 7,758,855, which are herein incorporated by reference). To generate a plasmid system for expression of *Y. pestis* F1-V fusion protein, a previously published synthetic construct of *Y. pestis* F1-V fusion (GenBank Accession No. AY924380.1) was modified (FIG. 1). The low-copy-number plasmid pGB-2, which has been used successfully in Ty21a (Osorio et al., *Infect Immun* 77(4):1475-1482, 2009; Xu et al., *Infect Immun* 70(8):4414-4423, 2002), was used as the backbone for plasmid construction. The synthetic F1-V fusion was cloned downstream from the htrA promoter in plasmid pGB-2 (FIG. 2).

Figure 2:
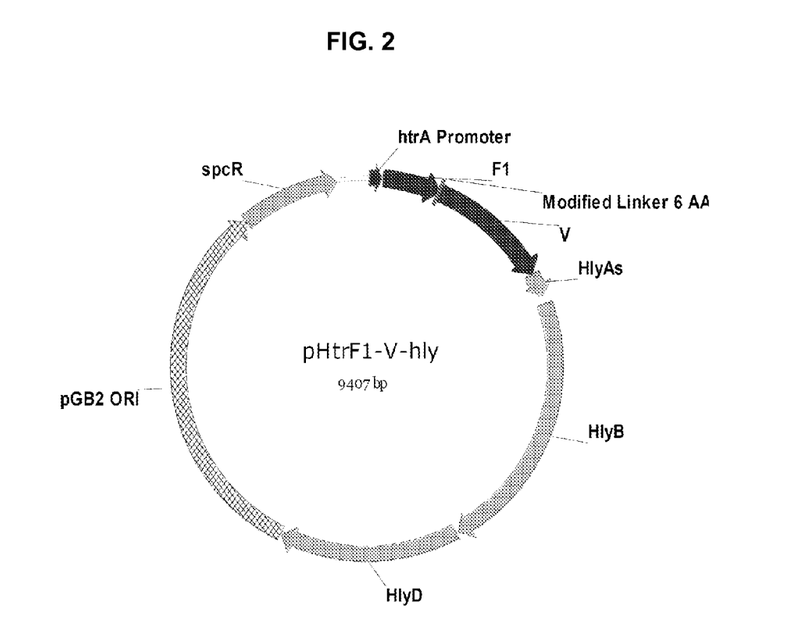
FIG. 2 is a schematic representation of the plasmid pHtrF1-V-Hly (9407 bp), which consists of a plague F1-V gene fusion construct cloned into low copy plasmid pGB-2. The pGB-2 origin of replication (ORI) is situated adjacent to the selectable spectinomycin resistance gene (spcR). The synthetic gene fusion insert consists of the htrA promoter linked to the F1-V genes, which are fused to each other via a modified linker sequence, and to the HlyA extracellular secretion signal (HlyAs). The plasmid also includes the coding sequences for the secretion machinery proteins HlyB and HlyD.

To induce extracellular expression, an in-frame genetic fusion of the synthetic F1-V fusion gene (lacking a stop codon) was created with the secretion signal peptide (last 66 amino acids) of the *E. coli* alpha-hemolysin protein HlyA (FIG. 1 and FIG. 2). The genes encoding HlyB and HlyD, necessary components of the HlyA transport apparatus, were also included on the plasmid vector (FIG. 2).

Figure 3:
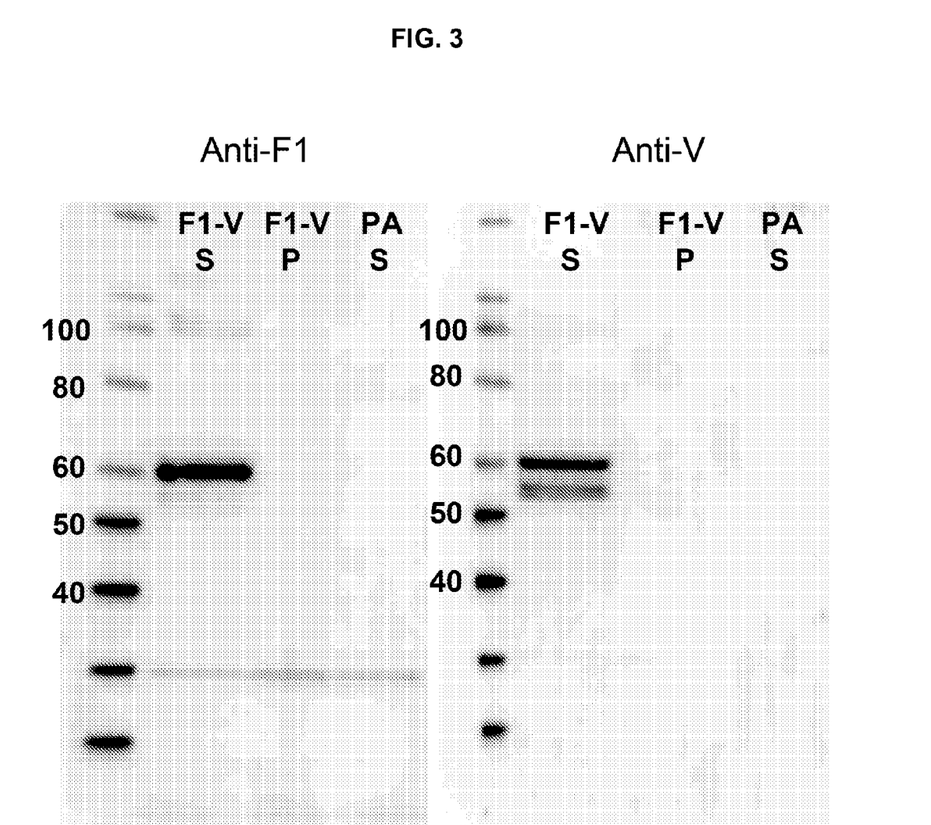
FIG. 3 shows analysis of protein extracts by SDS-PAGE. *Salmonella* Typhi Ty21a was transformed with either pHtrF1-V-hly (containing *Y. pestis* F1-V fusion protein) or pHtr-PAcm-hly (containing *B. anthracis* protective antigen (PA); as described by Osorio et al., *Infect Immun* 77(4):1475-1482, 2009). Cultures were grown overnight and both the culture supernatants (S) and cell pellets (P) were collected. Protein extracts were analyzed by SDS-PAGE and probed with commercially available anti-F1 or anti-V monoclonal antibodies.

DNA Sequence of the F1-V Fusion DNA Insert Cloned into Plasmid pHtrF1-V-Hly:

(SEQ ID NO: 1)
tggacttttgtaaagatggacaataaatttttactttttccagaaactt tattccggaacttcgcgttataaaatgaatctgacgtacacagcaattt taaggagaggacatatggcagatttaactgcaagcaccactgcaacggc aactcttgttgaaccagcccgcatcactcttacatataaggaaggcgct ccaattacaattatggacaatggaaacatcgatacagaattacttgttg gtacgcttactcttggcggctataaaacaggaaccactagcacatctgt taactttacagatgccgcgggtgatcccatgtacttaacatttacttct caggatggaaataaccaccaattcactacaaaagtgattggcaaggatt ctagagattttgatatctctcctaaggtaaacggtgagaaccttgtggg ggatgacgtcgtcttggctacgggcagccaggatttctttgttcgctca attggttccaaaggcggtaaacttgcagcaggtaaatacactgatgctg taaccgtaaccgtatctaaccaaggatccatcgaaggtcgtatgattag agcctacgaacaaaacccacaacattttattgaggatctagaaaaagtt agggtggaacaacttactggtcatggttcttcagttttagaagaattgg ttcagttagtcaaagataaaaatatagatatttccattaaatatgatcc cagaaaagattcggaggttttttgccaatagagtaattactgatgatatc gaattgctcaagaaaatcctagcttattttctacccgaggatgccattc ttaaaggcggtcattatgacaaccaactgcaaaatggcatcaagcgagt aaaagagttccttgaatcatcgccgaatacacaatgggaattgcgggcg ttcatggcagtaatgcacttctctttaaccgccgatcgtatcgatgatg atattttgaaagtgattgttgattcaatgaatcatcatggtgatgcccg tagcaagttgcgtgaagaattagctgagcttaccgccgaattaaagatt tattcagttattcaagccgaaattaataagcatctgtctagtagtggca ccataaatatccatgataaatccattaatctcatggataaaaatttata tggttatacagatgaagagattttttaaagccagcgcagagtacaaaatt ctcgagaaaatgcctcaaaccaccattcaggtggatgggagcgagaaaa aaatagtctcgataaaggactttcttggaagtgagaataaaagaaccgg ggcgttgggtaatctgaaaaactcatactcttataataaagataataat gaattatctcactttgccaccacctgctcggataagtccaggccgctca acgacttggttagccaaaaacaactcagctgtctgatattacatcacg ttttaattcagctattgaagcactgaaccgtttcattcagaaatatgat tcagtgatgcaacgtctgctagatgacacgtctggtaaatatgcatcaa cttatgcagacctggataatctgaatccattaattaatgaaatcagcaa aattatttcagctgcaggtaacttcgatgttaaggaggaaagatctgcc gcttcttattgcagttgtccggtaatgccagtgattttcatatggac ggaactcaataactttgaccgcatcagcataa For assessment of F1-V expression and secretion in S. Typhi Ty21a, Ty21a transformed with either pHtrF1-V-hly or the previously constructed plasmid encoding B. anthracis PA (Osorio et al., Infect Immun 77(4):1475-1482, 2009) were grown in culture medium with spectinomycin selection overnight and subsequently harvested by centrifugation. The supernatant fractions were concentrated approximately 10-fold. The pellet fractions were simultaneously lysed in a volume equal to that of the concentrated supernatants. Equal volumes of the supernatant and pellet fractions were analyzed via Western blot using commercially available monoclonal antibodies to either F1 or LcrV.

As shown in FIG. 3, the results clearly demonstrate that Ty21a transformed with pHtrF1-V produce and secrete the F1-V fusion protein. In fact, no F1-V is detectable in the pellet fraction. Based on the translated DNA sequence, the predicted molecular mass of the F1-V fusion protein is approximately 58 kDa. The observed slightly higher molecular mass of F1-V secreted from Ty21a is likely a reflection of the addition of the 66 amino acid secretion signal HlyA. Detection of F1-V using the anti-LcrV antibody detects a second product that is approximately 55 to 58 kDa. This band likely represents F1-V that has been cleaved of HlyA.

Example 2

Immunogenicity of Vaccine Constructs in Mice

This example describes the immunogenicity of *Salmonella* Typhi Ty21a harboring the F1-V fusion expression construct, as measured by serum IgG titers and cytokine expression of stimulated splenocytes.

The ability of Ty21a expressing F1-V to induce a protective immune response was examined by immunization of A/J mice. Groups of ten 6- to 8-week-old mice were immunized via the intraperitoneal (i.p.) route with three biweekly doses containing Ty21a producing F1-V or the previously constructed anthrax PA. A third group of mice received a 1:1 mixture of Ty21a producing F1-V and Ty21a producing PA. Control mice received three doses of Ty21a transformed with the empty pGB-2 vector. Immunized mice received $2\text{-}5\times10^7$ CFU per dose. Serum and spleens were collected one week following the third and final immunization. Total circulating F1-V- and PA-specific IgG titers were analyzed by ELISA.

Figure 4:
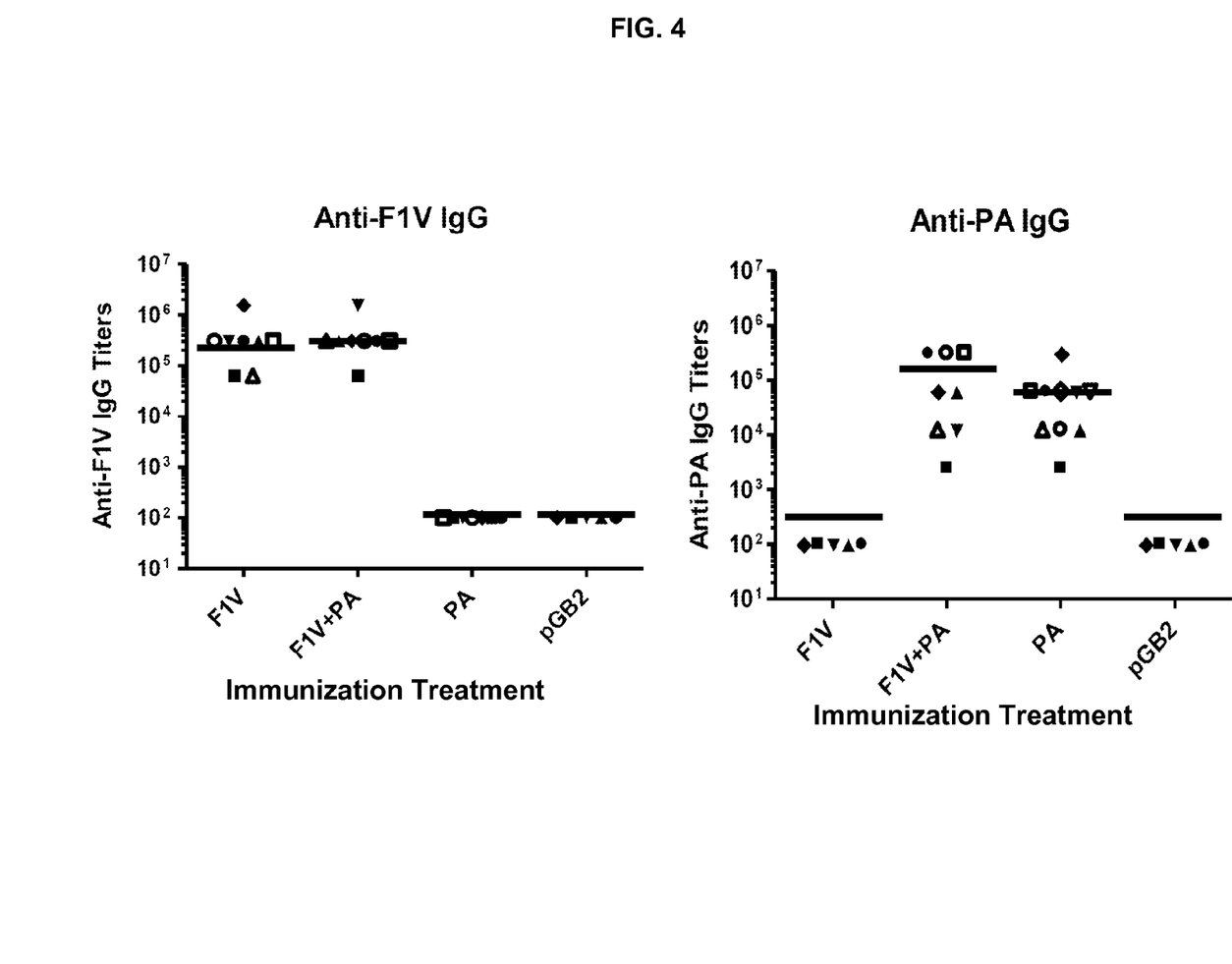
FIG. 4 is a pair of graphs showing total serum IgG titers against the F1-V and PA antigens. Groups of ten 6- to 8-week-old mice were immunized via the intraperitoneal (i.p.) route with three biweekly doses containing *Salmonella* Typhi Ty21a producing F1-V or the previously constructed anthrax PA. A third group of mice received a 1:1 mixture of Ty21a producing F1-V and Ty21a producing PA. Control mice received three doses of Ty21a transformed with the empty pGB-2 vector. Immunized mice received $2-5 \times 10^7$ colony forming units (CFU) per dose. Serum was collected one week following the third and final immunization. Total circulating F1-V- and PA-specific IgG titers were analyzed by ELISA.

Expression of F1-V fusion in Ty21a resulted in high anti-F1-V serum IgG titers in mice, averaging geometric mean titers of nearly 500,000 (FIG. 4). Concomitant immunization with Ty21a expressing F1-V and Ty21a expressing PA resulted in high anti-F1-V and anti-PA IgG titers in mice. Ty21a control strains expressing empty vector pGB2 resulted in no circulating anti-F1-V or anti-PA IgG.

Figure 5:
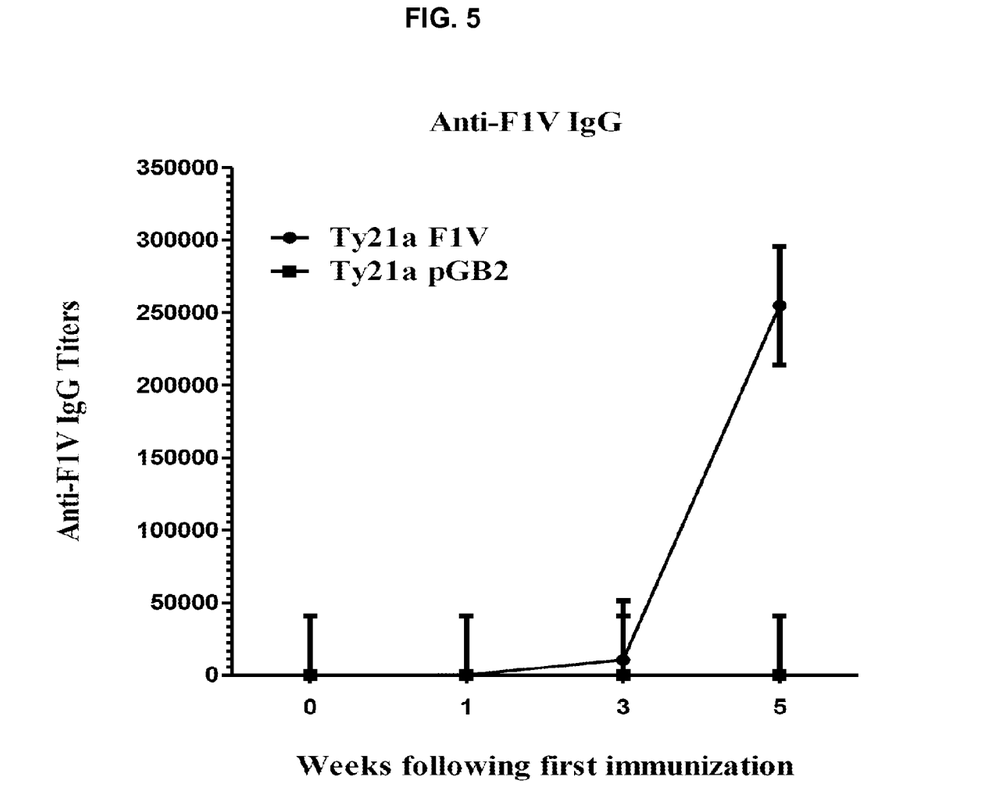
FIG. 5 is a graph showing total serum IgG titers against the F1-V antigen. Eight-week old mice (n=5 per group per time point) were immunized three times via the i.p. route every two weeks with *Salmonella* Typhi Ty21a transformed with the F1-V plasmid or with the empty pGB-2 vector. Mice received $2-5 \times 10^7$ CFU per dose at weeks 0, 2 and 4. Serum from five mice per treatment was collected at weeks 0, 1, 3 and 5. Total circulating F1-V-specific IgG titers were analyzed by ELISA.
Figure 6A:
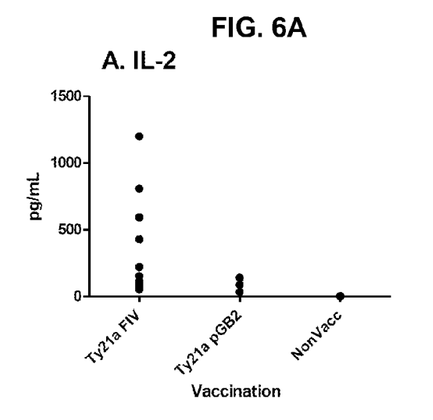
FIGS. 6A-6D are graphs showing splenocyte in vitro recall responses to rF1-V. Groups of ten 6- to 8-week-old mice were either not immunized, or immunized via the intraperitoneal (i.p.) route with three biweekly doses containing Ty21a producing F1-V or empty vector pGB2. Immunized mice received $2 \times 10^7$ CFU per dose. Splenocytes were harvested one week following the third and final immunization and stimulated in vitro with rF1-V for 72 hours. Culture supernatants were harvested and analyzed for cytokines.
Figure 6B:
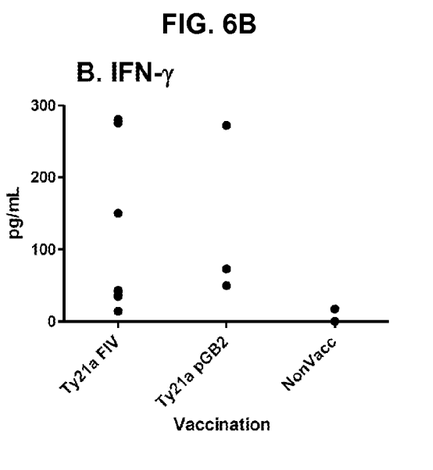
Figure 6C:
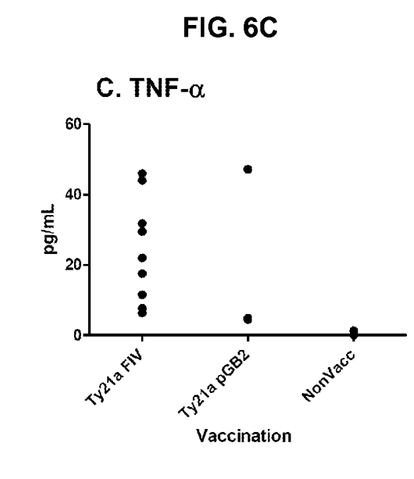
Figure 6D:
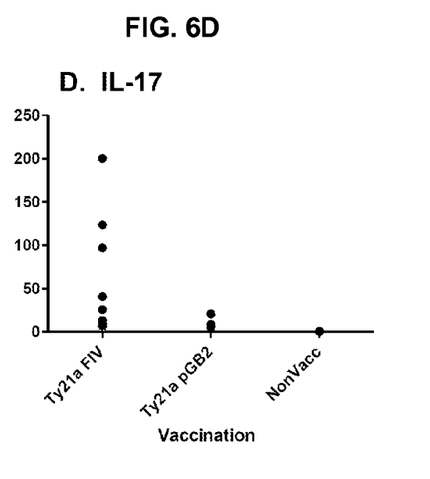

In a subsequent experiment, total serum IgG titers were determined in 8-week old mice immunized three times (i.p.) every two weeks with Ty21a transformed with the F1-V plasmid or with the empty pGB-2 plasmid. Immunized mice received $2\text{-}5\times10^7$ CFU per dose at weeks 0, 2 and 4, and serum was collected at weeks 0, 1, 3 and 5. Total circulating F1-V-specific IgG titers were analyzed by ELISA. The results indicated that three immunizations produced high anti-F1-V IgG titers in mice (FIG. 5).

Several prior studies have suggested that next-generation plague vaccines should aim to induce both *Y. pestis*-specific Ig and cellular mediated immune (CMI) responses. With this in mind, the cytokine response of harvested splenocytes stimulated in vitro with rF1-V for 72 hours was measured.

Groups of ten 6- to 8-week-old mice were either not immunized (control), or immunized i.p. with three biweekly doses containing Ty21a producing F1-V or empty vector pGB2. Immunized mice received $2\text{-}5\times10^7$ CFU per dose. Splenocytes were harvested one week following the third and final immunization and stimulated in vitro with rF1-V for 72 hours. Culture supernatants were harvested and analyzed for cytokine production.

As shown in FIGS. 6A-6D, cytokine (IL-2, IFN-γ, TNF-α, and IL-17) recall responses to rF1-V were variable. Splenocytes from non-immunized mice did not secrete IL-2, IFN-γ, TNF-α, or IL-17 when stimulated with rF1-V. However, splenocytes from some mice immunized with Ty21a transformed with pHtrF1-V-hly expressed significant amounts of IL-2, IFN-γ, TNF-α, and IL-17. One mouse immunized with Ty21a transformed with pGB2 alone had significant IFN-γ and TNF-α recall responses to rF1-V.

Example 3

Method of Preventing or Inhibiting Infection by *Y. pestis*

This example describes an exemplary method that can be used to prevent or inhibit infection by *Y. pestis*, thereby preventing or inhibiting the developing plague in a subject at risk.

A subject that is at risk for infection by *Y. pestis* is selected for treatment. For example, the subject may be an individual living in an area where plague is endemic, or a subject that has come in contact with other plague victims. The subject is administered an immunogenic composition that includes a *Salmonella* Typhi Ty21a bacterium harboring a F1-V fusion protein expression construct. The F1-V expression plasmid includes a *Y. pestis* F1-V fusion protein coding sequence operably linked to an *E. coli* htrA promoter sequence, and an *E. coli* HlyA secretion signal peptide secretion signal peptide coding sequence fused in-frame with the F1-V fusion protein coding sequence (SEQ ID NO: 1). An appropriate therapeutically effective dose of the immunogenic composition can be selected by a skilled practitioner. In some examples, the dose is about $10^6$ to about $10^8$ CFU. The subject can be administered a single dose or multiple doses as needed in order to elicit a sufficient immune response against *Y. pestis*.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant nucleic acid molecule comprising a *Y. pestis* F1-V fusion protein coding sequence operably linked to an *E. coli* htrA promoter sequence, and further comprising an *E. coli* HlyA secretion signal peptide secretion signal peptide coding sequence fused in-frame with the F1-V fusion protein coding sequence, wherein the sequence of the nucleic acid molecule comprises SEQ ID NO: 1.

2. A plasmid comprising the recombinant nucleic acid molecule of claim 1, an origin of replication, a selectable marker and the *E. coli* HlyB and HlyD protein coding sequences.

3. A plasmid comprising the recombinant nucleic acid molecule of claim 1.

4. A recombinant nucleic acid molecule comprising a *Yersinia pestis* F1-V fusion protein coding sequence operably linked to an *Escherichia coli* htrA promoter sequence, wherein the nucleic acid molecule comprises a sequence at least 95% identical to nucleotides 1-1558 of SEQ ID NO: 1.

5. The recombinant nucleic acid molecule of claim 4, wherein the nucleic acid molecule comprises the sequence of nucleotides 1-1558 of SEQ ID NO: 1.

6. The recombinant nucleic acid molecule of claim 4, further comprising a secretion signal peptide coding sequence fused in-frame with the F1-V fusion protein coding sequence.

7. The recombinant nucleic acid molecule of claim 6, wherein the secretion signal peptide is the *E. coli* HlyA secretion signal peptide.

8. The recombinant nucleic acid molecule of claim 6, wherein the sequence of the nucleic acid molecule is at least 95% identical to SEQ ID NO: 1.

9. A plasmid comprising the recombinant nucleic acid molecule of claim 4.

10. The plasmid of claim 9, wherein the plasmid is a low-copy number plasmid.

11. The plasmid of claim 9, further comprising a selectable marker.

12. The plasmid of claim 11, wherein the selectable marker is an antibiotic resistance gene.

13. The plasmid of claim 9, further comprising the *E. coli* HlyB and HlyD protein coding sequences.

14. A *Salmonella Typhi* Ty21a bacterium comprising the recombinant nucleic acid molecule of claim 4.

15. An immunogenic composition comprising the *Salmonella Typhi* Ty21a bacterium of claim 14 and a pharmaceutically acceptable carrier.

16. The immunogenic composition of claim 15, wherein the composition is formulated for oral administration.

17. A method of eliciting an immune response against *Yersinia pestis* in a subject, comprising administering to the subject the *Salmonella Typhi* Ty21a bacterium of claim 14.

18. The method of claim 17, wherein the immune response is a protective immune response.

19. A method of reducing the risk of developing plague or treating plague in a subject, comprising administering to the subject the *Salmonella Typhi* Ty21a of claim 14.

* * * * *

SEQUENCE LISTING

```
<160> NUMBER OF SEQ ID NOS: 5

<210> SEQ ID NO 1
<211> LENGTH: 1747
<212> TYPE: DNA
<213> ORGANISM: Artificial Sequence
<220> FEATURE:
<223> OTHER INFORMATION: Synthetic polynucleotide
<220> FEATURE:
<221> NAME/KEY: promoter
<222> LOCATION: (1)..(112)
<220> FEATURE:
<221> NAME/KEY: CDS
<222> LOCATION: (113)..(562)
<223> OTHER INFORMATION: F1 antigen coding sequence
<220> FEATURE:
<221> NAME/KEY: CDS
<222> LOCATION: (563)..(580)
<223> OTHER INFORMATION: linker sequence
<220> FEATURE:
<221> NAME/KEY: CDS
<222> LOCATION: (581)..(1558)
<223> OTHER INFORMATION: V antigen coding sequence
<220> FEATURE:
<221> NAME/KEY: CDS
<222> LOCATION: (1559)..(1747)
<223> OTHER INFORMATION: hlyA secretion signal sequence

<400> SEQUENCE: 1 tggactttg taaagatgga caataaattt ttacttttc cagaaacttt attccggaac        60
ttcgcgttat aaaatgaatc tgacgtacac agcaatttta aggagaggac at atg gca    118
                                                          Met Ala
                                                            1 gat tta act gca agc acc act gca acg gca act ctt gtt gaa cca gcc      166
Asp Leu Thr Ala Ser Thr Thr Ala Thr Ala Thr Leu Val Glu Pro Ala
         5                   10                  15 cgc atc act ctt aca tat aag gaa ggc gct cca att aca att atg gac      214
Arg Ile Thr Leu Thr Tyr Lys Glu Gly Ala Pro Ile Thr Ile Met Asp
     20                  25                  30 aat gga aac atc gat aca gaa tta ctt gtt ggt acg ctt act ctt ggc      262
Asn Gly Asn Ile Asp Thr Glu Leu Leu Val Gly Thr Leu Thr Leu Gly
 35                  40                  45                  50
```

-continued

| | | |
|---|---|---|
| ggc tat aaa aca gga acc act agc aca tct gtt aac ttt aca gat gcc<br>Gly Tyr Lys Thr Gly Thr Thr Ser Thr Ser Val Asn Phe Thr Asp Ala<br>    55                  60                  65 | | 310 |
| gcg ggt gat ccc atg tac tta aca ttt act tct cag gat gga aat aac<br>Ala Gly Asp Pro Met Tyr Leu Thr Phe Thr Ser Gln Asp Gly Asn Asn<br>        70                  75                  80 | | 358 |
| cac caa ttc act aca aaa gtg att ggc aag gat tct aga gat ttt gat<br>His Gln Phe Thr Thr Lys Val Ile Gly Lys Asp Ser Arg Asp Phe Asp<br>            85                  90                  95 | | 406 |
| atc tct cct aag gta aac ggt gag aac ctt gtg ggg gat gac gtc gtc<br>Ile Ser Pro Lys Val Asn Gly Glu Asn Leu Val Gly Asp Asp Val Val<br>        100                 105                 110 | | 454 |
| ttg gct acg ggc agc cag gat ttc ttt gtt cgc tca att ggt tcc aaa<br>Leu Ala Thr Gly Ser Gln Asp Phe Phe Val Arg Ser Ile Gly Ser Lys<br>115                 120                 125                 130 | | 502 |
| ggc ggt aaa ctt gca gca ggt aaa tac act gat gct gta acc gta acc<br>Gly Gly Lys Leu Ala Ala Gly Lys Tyr Thr Asp Ala Val Thr Val Thr<br>                135                 140                 145 | | 550 |
| gta tct aac caa gga tcc atc gaa ggt cgt atg att aga gcc tac gaa<br>Val Ser Asn Gln Gly Ser Ile Glu Gly Arg Met Ile Arg Ala Tyr Glu<br>            150                 155                 160 | | 598 |
| caa aac cca caa cat ttt att gag gat cta gaa aaa gtt agg gtg gaa<br>Gln Asn Pro Gln His Phe Ile Glu Asp Leu Glu Lys Val Arg Val Glu<br>        165                 170                 175 | | 646 |
| caa ctt act ggt cat ggt tct tca gtt tta gaa gaa ttg gtt cag tta<br>Gln Leu Thr Gly His Gly Ser Ser Val Leu Glu Glu Leu Val Gln Leu<br>    180                 185                 190 | | 694 |
| gtc aaa gat aaa aat ata gat att tcc att aaa tat gat ccc aga aaa<br>Val Lys Asp Lys Asn Ile Asp Ile Ser Ile Lys Tyr Asp Pro Arg Lys<br>195                 200                 205                 210 | | 742 |
| gat tcg gag gtt ttt gcc aat aga gta att act gat gat atc gaa ttg<br>Asp Ser Glu Val Phe Ala Asn Arg Val Ile Thr Asp Asp Ile Glu Leu<br>                215                 220                 225 | | 790 |
| ctc aag aaa atc cta gct tat ttt cta ccc gag gat gcc att ctt aaa<br>Leu Lys Lys Ile Leu Ala Tyr Phe Leu Pro Glu Asp Ala Ile Leu Lys<br>            230                 235                 240 | | 838 |
| ggc ggt cat tat gac aac caa ctg caa aat ggc atc aag cga gta aaa<br>Gly Gly His Tyr Asp Asn Gln Leu Gln Asn Gly Ile Lys Arg Val Lys<br>        245                 250                 255 | | 886 |
| gag ttc ctt gaa tca tcg ccg aat aca caa tgg gaa ttg cgg gcg ttc<br>Glu Phe Leu Glu Ser Ser Pro Asn Thr Gln Trp Glu Leu Arg Ala Phe<br>    260                 265                 270 | | 934 |
| atg gca gta atg cac ttc tct tta acc gcc gat cgt atc gat gat gat<br>Met Ala Val Met His Phe Ser Leu Thr Ala Asp Arg Ile Asp Asp Asp<br>275                 280                 285                 290 | | 982 |
| att ttg aaa gtg att gtt gat tca atg aat cat cat ggt gat gcc cgt<br>Ile Leu Lys Val Ile Val Asp Ser Met Asn His His Gly Asp Ala Arg<br>                295                 300                 305 | | 1030 |
| agc aag ttg cgt gaa gaa tta gct gag ctt acc gcc gaa tta aag att<br>Ser Lys Leu Arg Glu Glu Leu Ala Glu Leu Thr Ala Glu Leu Lys Ile<br>            310                 315                 320 | | 1078 |
| tat tca gtt att caa gcc gaa att aat aag cat ctg tct agt agt ggc<br>Tyr Ser Val Ile Gln Ala Glu Ile Asn Lys His Leu Ser Ser Ser Gly<br>        325                 330                 335 | | 1126 |
| acc ata aat atc cat gat aaa tcc att aat ctc atg gat aaa aat tta<br>Thr Ile Asn Ile His Asp Lys Ser Ile Asn Leu Met Asp Lys Asn Leu<br>    340                 345                 350 | | 1174 |
| tat ggt tat aca gat gaa gag att ttt aaa gcc agc gca gag tac aaa<br>Tyr Gly Tyr Thr Asp Glu Glu Ile Phe Lys Ala Ser Ala Glu Tyr Lys | | 1222 |

```
                355                 360                 365                 370
att ctc gag aaa atg cct caa acc acc att cag gtg gat ggg agc gag      1270
Ile Leu Glu Lys Met Pro Gln Thr Thr Ile Gln Val Asp Gly Ser Glu
                375                 380                 385 aaa aaa ata gtc tcg ata aag gac ttt ctt gga agt gag aat aaa aga      1318
Lys Lys Ile Val Ser Ile Lys Asp Phe Leu Gly Ser Glu Asn Lys Arg
                390                 395                 400 acc ggg gcg ttg ggt aat ctg aaa aac tca tac tct tat aat aaa gat      1366
Thr Gly Ala Leu Gly Asn Leu Lys Asn Ser Tyr Ser Tyr Asn Lys Asp
                405                 410                 415 aat aat gaa tta tct cac ttt gcc acc acc tgc tcg gat aag tcc agg      1414
Asn Asn Glu Leu Ser His Phe Ala Thr Thr Cys Ser Asp Lys Ser Arg
                420                 425                 430 ccg ctc aac gac ttg gtt agc caa aaa aca act cag ctg tct gat att      1462
Pro Leu Asn Asp Leu Val Ser Gln Lys Thr Thr Gln Leu Ser Asp Ile
435                 440                 445                 450 aca tca cgt ttt aat tca gct att gaa gca ctg aac cgt ttc att cag      1510
Thr Ser Arg Phe Asn Ser Ala Ile Glu Ala Leu Asn Arg Phe Ile Gln
                455                 460                 465 aaa tat gat tca gtg atg caa cgt ctg cta gat gac acg tct ggt aaa      1558
Lys Tyr Asp Ser Val Met Gln Arg Leu Leu Asp Asp Thr Ser Gly Lys
                470                 475                 480 tat gca tca act tat gca gac ctg gat aat ctg aat cca tta att aat      1606
Tyr Ala Ser Thr Tyr Ala Asp Leu Asp Asn Leu Asn Pro Leu Ile Asn
                485                 490                 495 gaa atc agc aaa att att tca gct gca ggt aac ttc gat gtt aag gag      1654
Glu Ile Ser Lys Ile Ile Ser Ala Ala Gly Asn Phe Asp Val Lys Glu
                500                 505                 510 gaa aga tct gcc gct tct tta ttg cag ttg tcc ggt aat gcc agt gat      1702
Glu Arg Ser Ala Ala Ser Leu Leu Gln Leu Ser Gly Asn Ala Ser Asp
515                 520                 525                 530 ttt tca tat gga cgg aac tca ata act ttg acc gca tca gca taa          1747
Phe Ser Tyr Gly Arg Asn Ser Ile Thr Leu Thr Ala Ser Ala
                535                 540

<210> SEQ ID NO 2
<211> LENGTH: 150
<212> TYPE: PRT
<213> ORGANISM: Artificial Sequence
<220> FEATURE:
<223> OTHER INFORMATION: Synthetic Construct

<400> SEQUENCE: 2

Met Ala Asp Leu Thr Ala Ser Thr Thr Ala Thr Ala Thr Leu Val Glu
1               5                   10                  15

Pro Ala Arg Ile Thr Leu Thr Tyr Lys Glu Gly Ala Pro Ile Thr Ile
                20                  25                  30

Met Asp Asn Gly Asn Ile Asp Thr Glu Leu Leu Val Gly Thr Leu Thr
            35                  40                  45

Leu Gly Gly Tyr Lys Thr Gly Thr Thr Ser Thr Ser Val Asn Phe Thr
    50                  55                  60

Asp Ala Ala Gly Asp Pro Met Tyr Leu Thr Phe Thr Ser Gln Asp Gly
65                  70                  75                  80

Asn Asn His Gln Phe Thr Thr Lys Val Ile Gly Lys Asp Ser Arg Asp
                85                  90                  95

Phe Asp Ile Ser Pro Lys Val Asn Gly Glu Asn Leu Val Gly Asp Asp
                100                 105                 110

Val Val Leu Ala Thr Gly Ser Gln Asp Phe Phe Val Arg Ser Ile Gly
            115                 120                 125
```

Ser Lys Gly Gly Lys Leu Ala Ala Gly Lys Tyr Thr Asp Ala Val Thr
        130                 135                 140

Val Thr Val Ser Asn Gln
145                 150

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Gly Ser Ile Glu Gly Arg
1               5

<210> SEQ ID NO 4
<211> LENGTH: 326
<212> TYPE: PRT
<213> ORGANISM: Artificial Sequence
<220> FEATURE:
<223> OTHER INFORMATION: Synthetic Construct

<400> SEQUENCE: 4

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr

```
                    260                 265                 270
Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 5
<211> LENGTH: 62
<212> TYPE: PRT
<213> ORGANISM: Artificial Sequence
<220> FEATURE:
<223> OTHER INFORMATION: Synthetic Construct

<400> SEQUENCE: 5

Tyr Ala Ser Thr Tyr Ala Asp Leu Asp Asn Leu Asn Pro Leu Ile Asn
1               5                   10                  15

Glu Ile Ser Lys Ile Ile Ser Ala Ala Gly Asn Phe Asp Val Lys Glu
            20                  25                  30

Glu Arg Ser Ala Ala Ser Leu Leu Gln Leu Ser Gly Asn Ala Ser Asp
        35                  40                  45

Phe Ser Tyr Gly Arg Asn Ser Ile Thr Leu Thr Ala Ser Ala
    50                  55                  60
```